(12) United States Patent
Butler et al.

(10) Patent No.: US 8,348,949 B2
(45) Date of Patent: Jan. 8, 2013

(54) SINGLE-SIDED DYNAMIC SPINE PLATES

(75) Inventors: Michael S. Butler, St. Charles, IL (US); Brian D. Hartsell, Aurora, IL (US)

(73) Assignee: Life Spine, Inc., Hoffman Estates, IL (US)

( * ) Notice: Subject to any disclaimer, the term of this patent is extended or adjusted under 35 U.S.C. 154(b) by 593 days.

(21) Appl. No.: 12/550,013

(22) Filed: Aug. 28, 2009

(65) Prior Publication Data

US 2010/0228291 A1   Sep. 9, 2010

Related U.S. Application Data

(60) Provisional application No. 61/092,836, filed on Aug. 29, 2008.

(51) Int. Cl.
*A61B 17/70* (2006.01)
(52) U.S. Cl. .......................................... 606/71; 606/259
(58) Field of Classification Search .................... 606/70, 606/71, 60, 246–331
See application file for complete search history.

(56) References Cited

U.S. PATENT DOCUMENTS

| | | | |
|---|---|---|---|
| 2,401,856 A | 6/1946 | Brock | |
| 3,741,205 A | 6/1973 | Markolf et al. | |
| 4,388,921 A | 6/1983 | Sutter et al. | |
| 4,794,918 A | 1/1989 | Wolter | |
| 4,808,185 A | 2/1989 | Penenberg et al. | |
| 5,364,399 A | 11/1994 | Lowery et al. | |
| 5,534,027 A | 7/1996 | Hodorek | |
| 5,607,426 A | 3/1997 | Ralph et al. | |
| 5,616,142 A * | 4/1997 | Yuan et al. | 606/71 |
| 5,620,443 A | 4/1997 | Gertzbein et al. | |
| 5,803,277 A | 9/1998 | Alvarez-Momoitio | |
| 5,951,558 A | 9/1999 | Fiz | |

(Continued)

FOREIGN PATENT DOCUMENTS

CH       674927 A5    8/1990

(Continued)

OTHER PUBLICATIONS

International Preliminary Report on Patentability for International Application No. PCT/US2009/055425, date mailed Oct. 9, 2010, 9 pages.

(Continued)

*Primary Examiner* — Kevin T Truong
*Assistant Examiner* — Christopher Beccia
(74) *Attorney, Agent, or Firm* — Foley & Lardner LLP

(57) ABSTRACT

A dynamic spine plate is formed with only a single row of bone screw bores that extend along a generally superior/inferior axis of the spine plate, providing a single-sided dynamic spine plate. The single-sided dynamic spine plate is formed from a plurality of spine plate components that are coupled dynamically to one another. This provides a modular, single-sided dynamic spine plate. The spine plate components are coupled dynamically to one another via socket and projection interfaces, the socket and projections interfaces incorporating resilient coupling and retention structures that allow limited movement of the spine plate components relative to one another. This provides for dynamic extension of the spine plate components relative to one another. The resilient coupling structure connects the spine plate components, providing a self-biased, snap fit coupling of spine plate components. Rotation stabilizers may be provide on the present single-sided dynamic spine plate that provide rotational stability to the spine plate in addition to the bone screws that will attach the spine plate to the vertebrae.

19 Claims, 16 Drawing Sheets

U.S. PATENT DOCUMENTS

| | | | | |
|---|---|---|---|---|
| 6,017,345 | A * | 1/2000 | Richelsoph | 606/70 |
| 6,139,550 | A | 10/2000 | Michelson | |
| 6,152,927 | A | 11/2000 | Farris et al. | |
| 6,193,721 | B1 | 2/2001 | Michelson | |
| 6,224,602 | B1 | 5/2001 | Hayes | |
| 6,228,085 | B1 | 5/2001 | Theken et al. | |
| 6,235,034 | B1 | 5/2001 | Bray | |
| 6,258,089 | B1 | 7/2001 | Campbell et al. | |
| 6,273,889 | B1 | 8/2001 | Richelsoph | |
| 6,306,136 | B1 | 10/2001 | Baccelli | |
| 6,364,881 | B1 | 4/2002 | Apgar et al. | |
| 6,398,783 | B1 | 6/2002 | Michelson | |
| 6,402,756 | B1 | 6/2002 | Ralph et al. | |
| 6,413,259 | B1 | 7/2002 | Lyons et al. | |
| 6,428,542 | B1 | 8/2002 | Michelson | |
| 6,454,769 | B2 | 9/2002 | Wagner et al. | |
| 6,503,250 | B2 | 1/2003 | Paul | |
| 6,533,786 | B1 | 3/2003 | Needham et al. | |
| 6,599,290 | B2 | 7/2003 | Bailey et al. | |
| 6,602,257 | B1 | 8/2003 | Thramann | |
| 6,620,163 | B1 | 9/2003 | Michelson | |
| 6,669,700 | B1 | 12/2003 | Farris et al. | |
| 6,695,846 | B2 | 2/2004 | Richelsoph et al. | |
| 6,854,919 | B2 | 2/2005 | Neumann et al. | |
| 6,872,210 | B2 | 3/2005 | Hearn | |
| 6,974,460 | B2 | 12/2005 | Carbone et al. | |
| 7,318,461 | B2 | 1/2008 | Zeller | |
| 7,318,825 | B2 | 1/2008 | Butler et al. | |
| 7,479,143 | B2 * | 1/2009 | Suh et al. | 606/71 |
| 7,666,185 | B2 * | 2/2010 | Ryan et al. | 606/71 |
| 7,806,911 | B2 * | 10/2010 | Peckham | 606/248 |
| 7,842,037 | B2 * | 11/2010 | Schulze | 606/71 |
| 7,951,151 | B2 | 5/2011 | Butler et al. | |
| 7,988,691 | B2 * | 8/2011 | Schulze et al. | 606/71 |
| 2001/0041894 | A1 | 11/2001 | Campbell et al. | |
| 2002/0045896 | A1 | 4/2002 | Michelson | |
| 2002/0045899 | A1 | 4/2002 | Errico et al. | |
| 2002/0111630 | A1 | 8/2002 | Ralph et al. | |
| 2002/0120273 | A1 | 8/2002 | Needham et al. | |
| 2002/0128655 | A1 | 9/2002 | Michelson | |
| 2002/0143336 | A1 | 10/2002 | Hearn | |
| 2002/0147450 | A1 | 10/2002 | LeHuec et al. | |
| 2002/0151899 | A1 | 10/2002 | Bailey et al. | |
| 2002/0183754 | A1 | 12/2002 | Michelson | |
| 2002/0183755 | A1 | 12/2002 | Michelson | |
| 2002/0183756 | A1 | 12/2002 | Michelson | |
| 2002/0183757 | A1 | 12/2002 | Michelson | |
| 2002/0188296 | A1 | 12/2002 | Michelson | |
| 2003/0023242 | A1 | 1/2003 | Harrington, Jr. | |
| 2003/0040749 | A1 | 2/2003 | Grabowski et al. | |
| 2003/0060828 | A1 | 3/2003 | Michelson | |
| 2003/0083658 | A1 | 5/2003 | Hawkes et al. | |
| 2003/0105462 | A1 | 6/2003 | Haider | |
| 2004/0034356 | A1 | 2/2004 | LeHuec et al. | |
| 2004/0068319 | A1 | 4/2004 | Cordaro | |
| 2004/0087951 | A1 | 5/2004 | Khalili | |
| 2004/0102773 | A1 | 5/2004 | Morrison et al. | |
| 2004/0106924 | A1 | 6/2004 | Ralph et al. | |
| 2004/0122426 | A1 | 6/2004 | Michelson | |
| 2004/0127896 | A1 | 7/2004 | Lombardo et al. | |
| 2004/0127897 | A1 | 7/2004 | Freid et al. | |
| 2004/0127899 | A1 | 7/2004 | Konieczynski et al. | |
| 2004/0181226 | A1 | 9/2004 | Michelson | |
| 2004/0181229 | A1 | 9/2004 | Michelson | |
| 2004/0186476 | A1 | 9/2004 | Michelson | |
| 2004/0204712 | A1 | 10/2004 | Kolb et al. | |
| 2004/0220571 | A1 | 11/2004 | Assaker et al. | |
| 2004/0220572 | A1 | 11/2004 | Michelson | |
| 2004/0236335 | A1 | 11/2004 | Michelson | |
| 2005/0004574 | A1 | 1/2005 | Muckter | |
| 2005/0027297 | A1 | 2/2005 | Michelson | |
| 2005/0027298 | A1 | 2/2005 | Michelson | |
| 2005/0033298 | A1 | 2/2005 | Hawkes et al. | |
| 2005/0043732 | A1 | 2/2005 | Dalton | |
| 2005/0059971 | A1 | 3/2005 | Michelson | |
| 2005/0075699 | A1 | 4/2005 | Olson et al. | |
| 2005/0137597 | A1 | 6/2005 | Butler et al. | |
| 2005/0149026 | A1 | 7/2005 | Butler et al. | |
| 2005/0216010 | A1 | 9/2005 | Michelson | |
| 2006/0116683 | A1 | 6/2006 | Barrall et al. | |
| 2006/0224241 | A1 | 10/2006 | Butler et al. | |
| 2006/0235398 | A1 * | 10/2006 | Farris et al. | 606/69 |
| 2006/0264941 | A1 * | 11/2006 | Lins | 606/61 |
| 2007/0118122 | A1 | 5/2007 | Butler et al. | |
| 2007/0233117 | A1 * | 10/2007 | Butler et al. | 606/69 |
| 2007/0293864 | A1 * | 12/2007 | Reimels et al. | 606/69 |
| 2008/0108998 | A1 * | 5/2008 | Lindemann | 606/71 |
| 2008/0114361 | A1 | 5/2008 | Butler et al. | |
| 2008/0208263 | A1 | 8/2008 | Butler et al. | |
| 2009/0326589 | A1 * | 12/2009 | Lemoine et al. | 606/280 |

FOREIGN PATENT DOCUMENTS

| | | |
|---|---|---|
| DE | 29 33 141 A1 | 4/1980 |
| EP | 0 179 695 A1 | 4/1986 |
| EP | 0 313 762 A1 | 5/1989 |
| FR | 2 651 996 A3 | 3/1991 |
| WO | WO 91/03994 A1 | 4/1991 |
| WO | WO 95/30389 A1 | 11/1995 |
| WO | WO 96/03096 A1 | 2/1996 |
| WO | WO 96/23457 A1 | 8/1996 |
| WO | WO 2004/017837 A2 | 3/2004 |
| WO | WO 2005/062900 A2 | 7/2005 |

OTHER PUBLICATIONS

International Search Report for International Application No. PCT/US2009/055425, date mailed Oct. 13, 2009, 1 page.

* cited by examiner

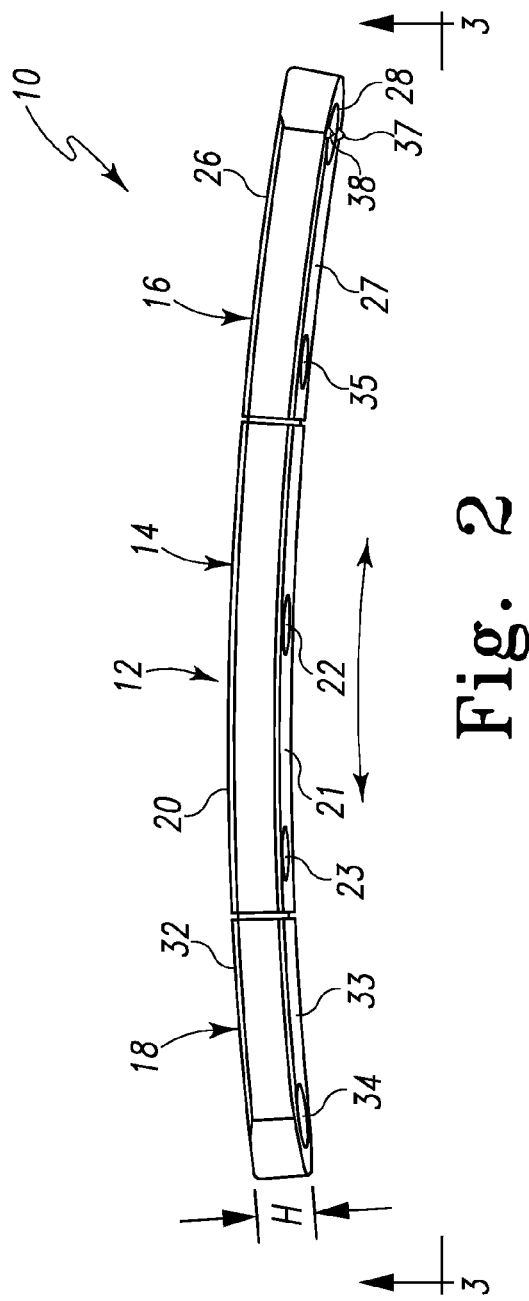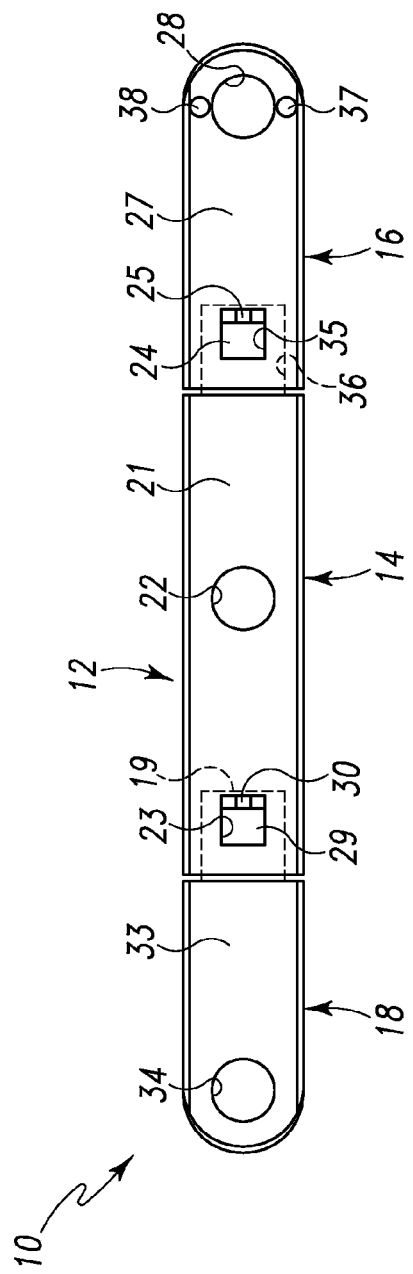

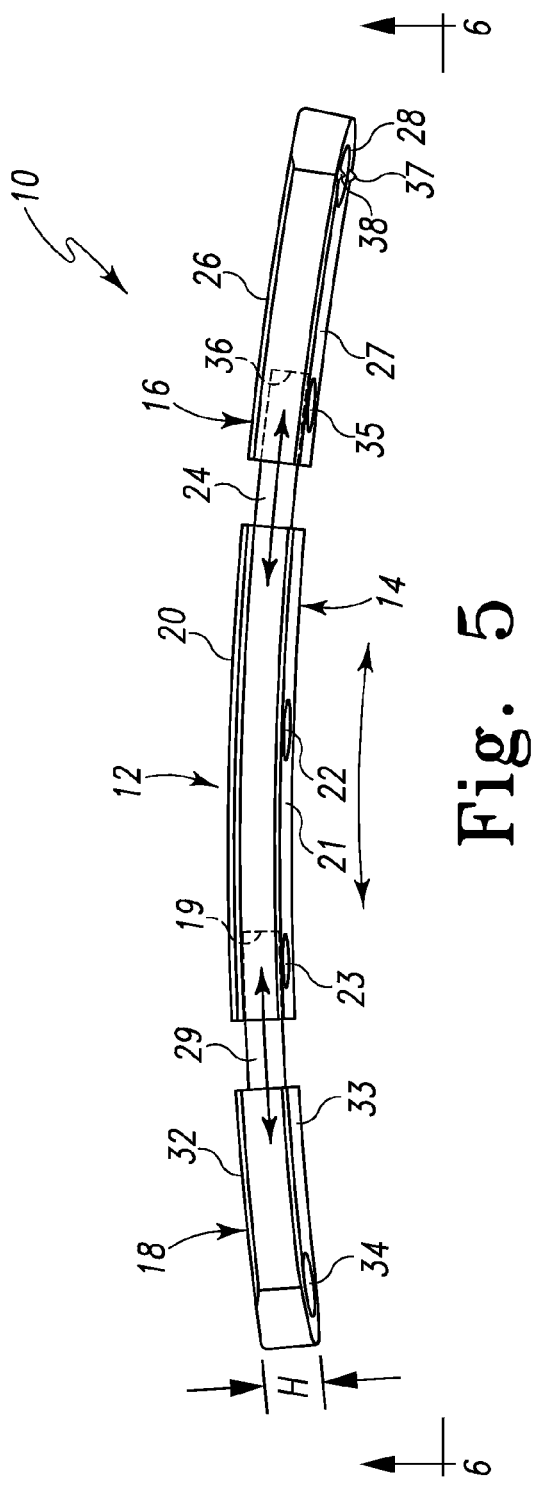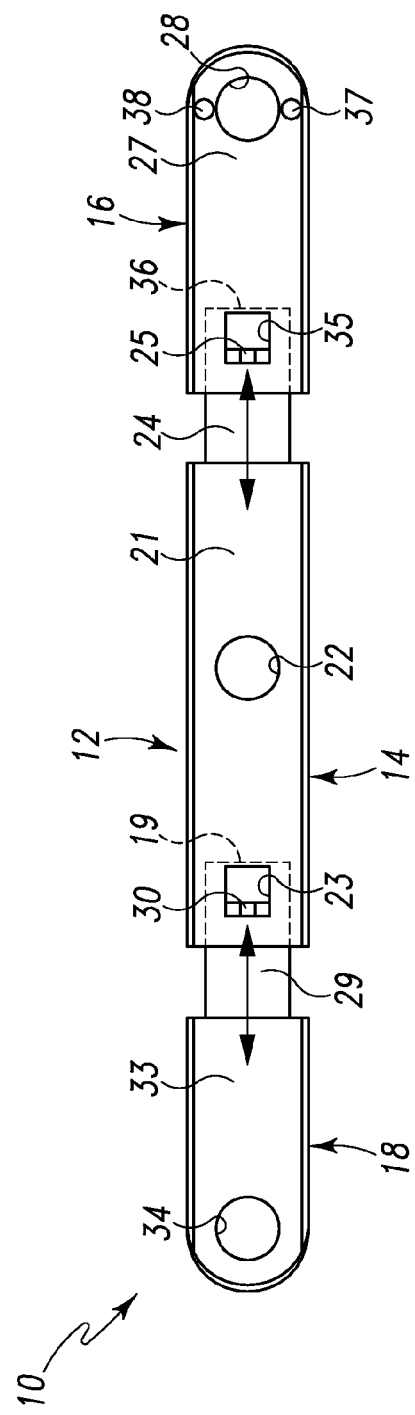

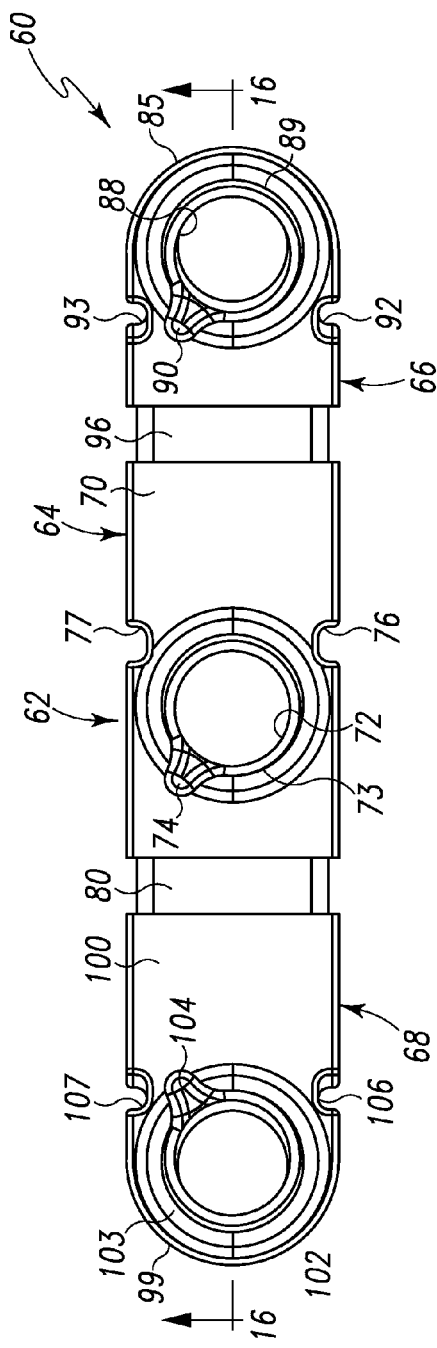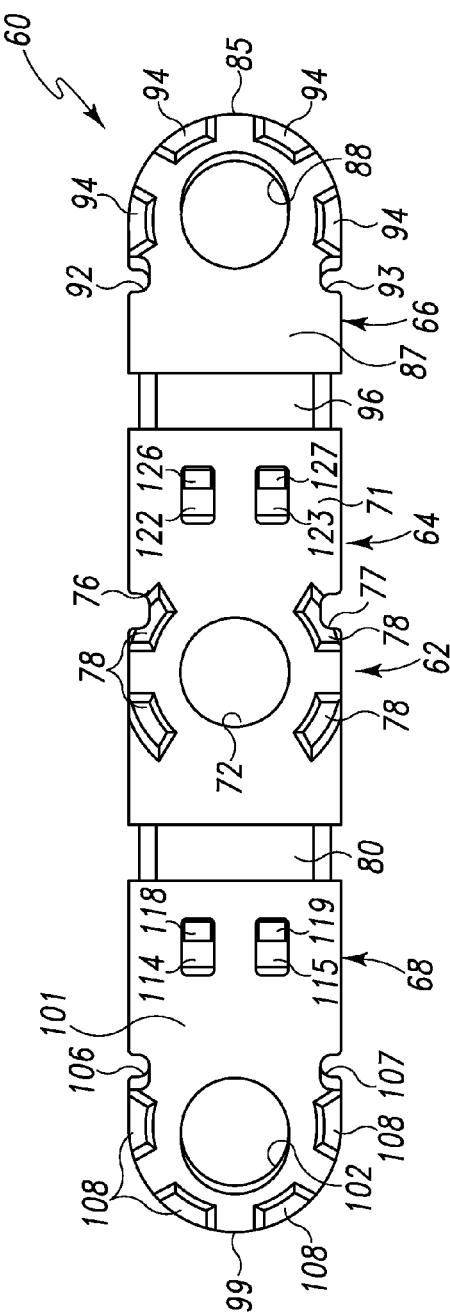

SINGLE-SIDED DYNAMIC SPINE PLATES

RELATED APPLICATIONS

This patent application claims the benefit of and/or priority to U.S. Provisional Patent Application Ser. No. 61/092,836 filed Aug. 29, 2008, entitled "Single Sided Dynamic Spine Plate" the entire contents of which is specifically incorporated herein by this reference.

BACKGROUND OF THE INVENTION

1. Field of the Invention

The present invention relates generally to devices for the internal fixation of the spine particularly within the fields of orthopedics and/or neurosurgery such as spinal implants for holding vertebral bones fixed relative to one another and, more particularly, to dynamic bone fixation implants for use in spinal surgical procedures for stabilizing the relative motion of vertebrae by temporarily or permanently immobilizing vertebrae of the spine.

2. Background Information

Spine plates have been used for many years to increase spine stability following single and multi-level spine surgery. Particularly, spine plates implanted during surgery for reasons such as disease, trauma, defect, accident or the like, are used to stabilize one or more spinal vertebrae. Stabilization leads to a proper healing or a desired outcome.

In some instances, it is desirous to cause the fusion of two adjacent vertebrae. If this is the case, the surgeon makes an incision to reach the spine. Tissues and muscles are retracted (spread apart) to reveal the proper level in the spine. The cartilaginous material or disc between the two vertebrae is removed and the bone surface abraded to encourage a bleeding surface. Blood from the bleeding surfaces is desired in order for the bones to fuse. The space between the adjacent vertebrae is filled with bone graft.

The spine plate is mounted to two or more vertebrae during the surgery. It is important during the mounting process that the spine plate be properly aligned on the vertebrae for receipt of the mounting screws. The spine plate must be fastened onto the vertebra via bone screws. This stabilizes the vertebrae in order to facilitate fusion and healing between the stabilized vertebrae. The bone screws are received in bores of the spine plate and hold the spine plate to the vertebra.

Such prior art spine plates, however, are configured to cover a large portion of the vertebral face and particularly of the anterior face of the vertebrae. They include at least two pairs of bone screws to be mounted to a vertebra, i.e. two bone screws in each vertebra and thus may be considered a double-sided spine plate (i.e. side-by-side spine plate) having a large width to accommodate the two pairs of bone screws. As such, these prior art spine plates cannot accommodate stabilization situations wherein it is desired to provide a spine plate on lateral sides of the vertebrae or in other situations where a smaller width spine plate is appropriate. There are instances where a spine plate of less width would be more appropriate and/or a spine plate fashioned for connection to other areas of the vertebrae.

In view of the above, it would thus be desirable to have a smaller width spine plate that is configured for attachment to various areas of a vertebra.

In view of the above, it would thus be desirable to have a dynamic spine plate that is configured for attachment to various areas of a vertebra.

SUMMARY OF THE INVENTION

A dynamic spine plate for vertebral stabilization is formed with a single row of fastening elements (e.g. bone screw bores) extending along a generally superior/inferior axis, providing a single-sided dynamic spine plate. The present single-sided dynamic spine plate is formed from a plurality of spine plate components that are coupled dynamically to one another. This provides a modular, single-sided dynamic spine plate.

In one form, the present single-sided dynamic spine plate utilizes a spine plate middle component and two spine plate end components. The spine plate end components are dynamic (i.e. they move) relative to the spine plate middle component.

In another form, the present single-sided dynamic spine plate utilizes a plurality of spine plate middle components and two spine plate end components to form a multi-level (n-level) single-sided dynamic spine plate.

In another form, a single-sided dynamic spine plate of a single level is achieved by utilizing two end components.

The spine plate components are coupled dynamically to one another via socket and projection interfaces. This allows for dynamic extension of two spine plate components relative to one another from the three or more spine plate components. The socket and projection interfaces incorporate a resilient coupling mechanism for connecting the spine plate components, providing a self-biased, snap fit coupling of spine plate components.

The present single-sided dynamic spine plate may be formed with a curve, bend or angle that mimics the curvature of the spine/vertebrae to which the present single-sided dynamic spine plate will be attached.

Rotation stabilizers may be provide on the present single-sided dynamic spine plate that provide rotational stability to the spine plate in addition to the bone screws that will attach the spine plate to the vertebrae. In one form, the rotation stabilizers comprise first and second protrusions on the dorsal end of the spine plate on the posterior side thereof. The protrusions can be spikes or be of other cross-sectional shapes (e.g. waffle patterns) that are oriented about or around the bone screw hole(s) of the plate. Other configurations of rotation stabilizers may be used. As well, rotation stabilizers may be used elsewhere along the present spine plate.

BRIEF DESCRIPTION OF THE DRAWINGS

The above mentioned and other features and objects of this invention, and the manner of attaining them, will become more apparent and the invention itself will be better understood by reference to the following description of embodiments of the invention taken in conjunction with the accompanying drawings, wherein:

FIG. 2 is a side view of the single-sided dynamic spine plate of FIG. 1 taken from the rear side of FIG. 1;

FIG. 3 is a bottom plan view of the single-sided dynamic plate of FIG. 1 taken along line 3-3 of FIG. 2;

FIG. 5 is a side view of the single-sided dynamic spine plate of FIG. 4;

FIG. 6 is a bottom plan view of the single-sided dynamic plate of FIG. 4 taken along line 6-6 of FIG. 5;

FIG. 14 is a top plan view of the single-sided dynamic spine plate of FIG. 13;

FIG. 15 is a bottom plan view of the single-sided dynamic spine plate of FIG. 13;

Like reference numerals indicate the same or similar parts throughout the several figures.

A description of the features, functions and/or configuration of the components depicted in the various figures will now be presented. It should be appreciated that not all of the features of the components of the figures are necessarily described. Some of these non discussed features as well as discussed features are inherent from the figures. Other non discussed features may be inherent in component geometry and/or configuration.

DETAILED DESCRIPTION OF THE PREFERRED EMBODIMENTS

Referring to the figures and particularly to FIGS. 1-7, there is depicted an embodiment of a single sided dynamic spine plate generally designated 10. The single sided dynamic spine plate 10 is formed of a suitable biocompatible material ("biomaterial") such as, for example, titanium, stainless steel, an alloy or the like. The single sided dynamic spine plate 10 (spine plate 10) is characterized by a multi-component body 12 fashioned as an elongated rectangle. The spine plate 10 is shown as a two level (2-L) spine plate but may be fashioned as a single level (1-L) to a multi-level or n-level (n-L) spine plate in accordance with the present principles.

Figure 1:
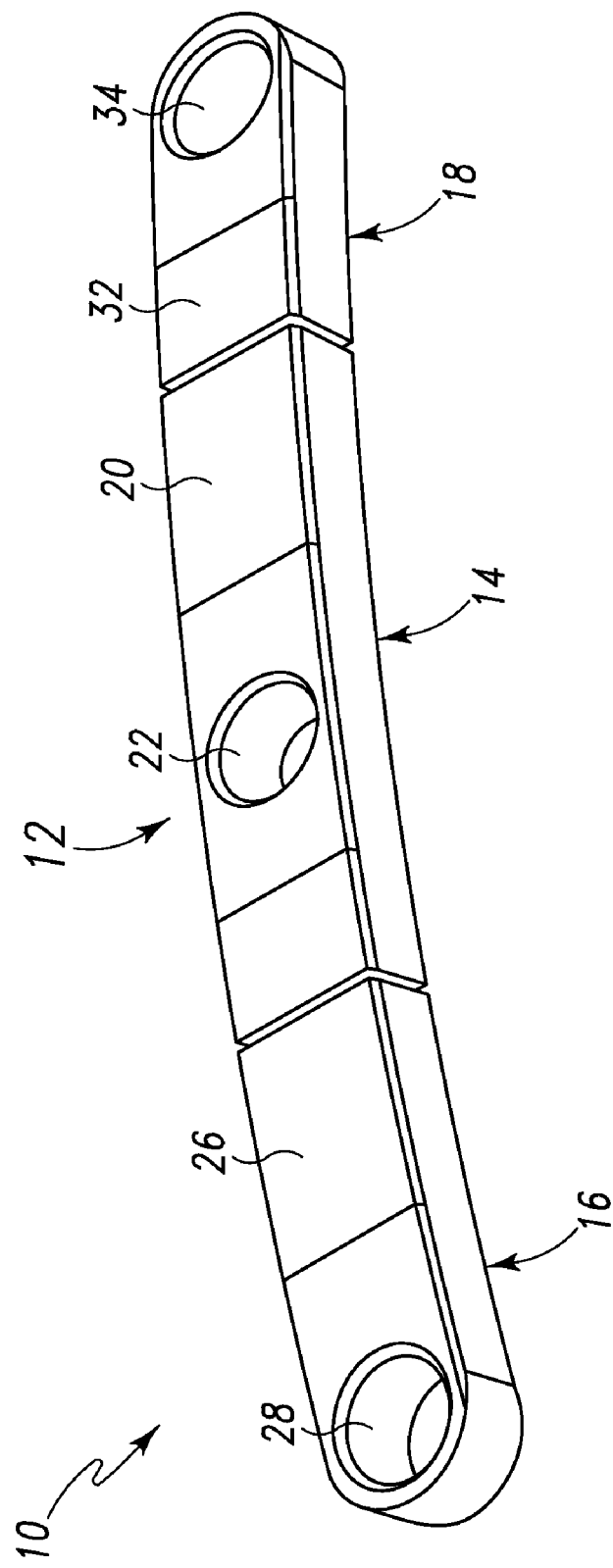
FIG. 1 is a perspective view of an embodiment of a single-sided dynamic spine plate fashioned in accordance with the present principles, the single-sided dynamic spine plate shown in an unexpanded, non-extended or closed position.
Figure 4:
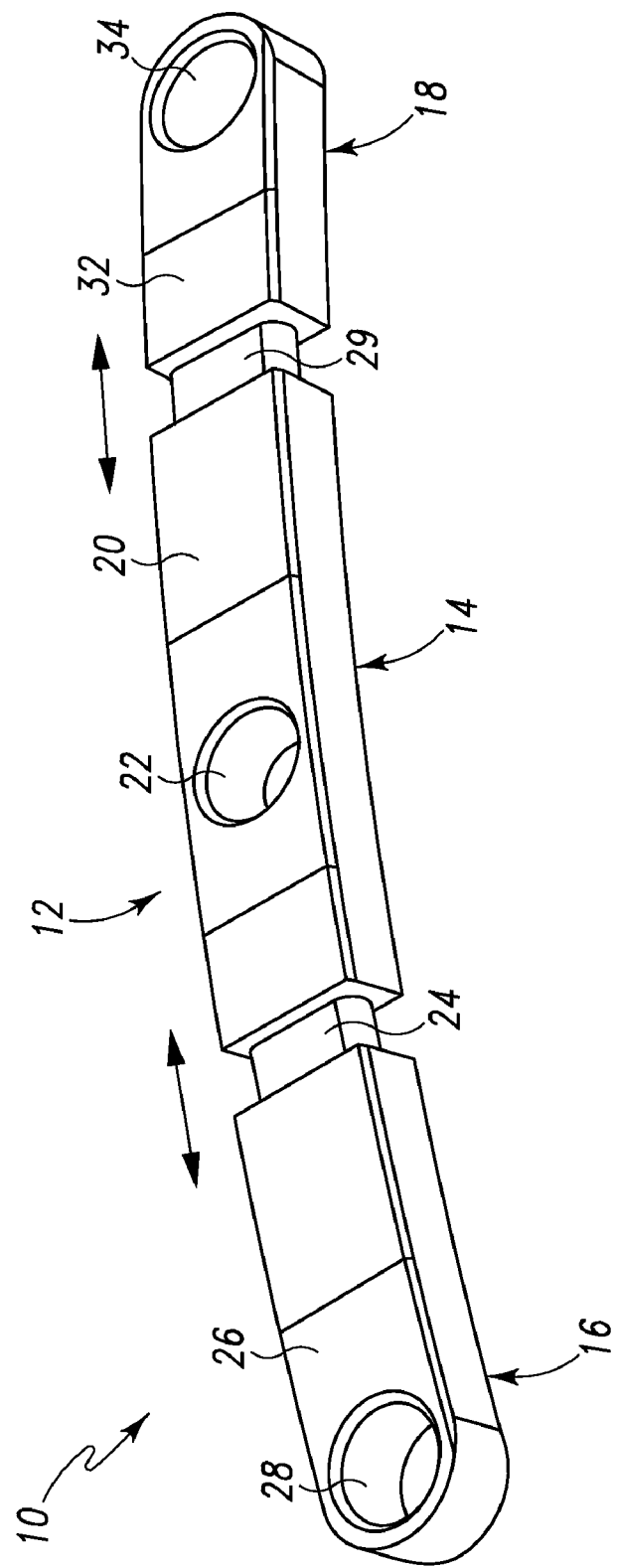
FIG. 4 is a perspective view of the single-sided dynamic spine plate of FIG. 1 shown in an expanded, extended or open position.

The body 12 is formed from a plurality of components and, in the embodiment shown in the figures, is formed of three components; a middle component, portion or section 14, a first end component, portion or section 16, and a second end component, portion or section 18. The body 12 defines a height or profile "H" (see, e.g. FIG. 2). As explained further below, the present spine plate 10 is dynamic in that it allows limited superior/inferior (axial) movement. In particular, the first and second end components 16, 18 are limitedly moveable relative to the middle component 14 (and/or the middle component 14 is movable relative to the first and second end components 16, 18. The spine plate 10 shown in FIGS. 1-3, however, is shown in a closed, un-extended or un-expanded position, wherein the first and second end components 16, 18 are abuttingly adjacent the middle component 14. In FIGS. 4-6 (discussed in detail below) the spine plate 10 is shown in an open, extended or expanded position wherein the first and second end components 16, 18 are a distance from the middle component 14. It should be appreciated that the open position shown in FIGS. 4-6 is only one open position of a possible plurality of open positions for the spine plate 10 (i.e. distances between the end components 16, 18 and the middle component 14). Ideally, end components 16 and 18 are identical or constitute the same piece. In this manner, two end components 16, 18 can be joined to provide a single level (1-L) spine plate (not shown in the figures) and connecting in the manner described herein with respect to the middle component 14.

Figure 7:
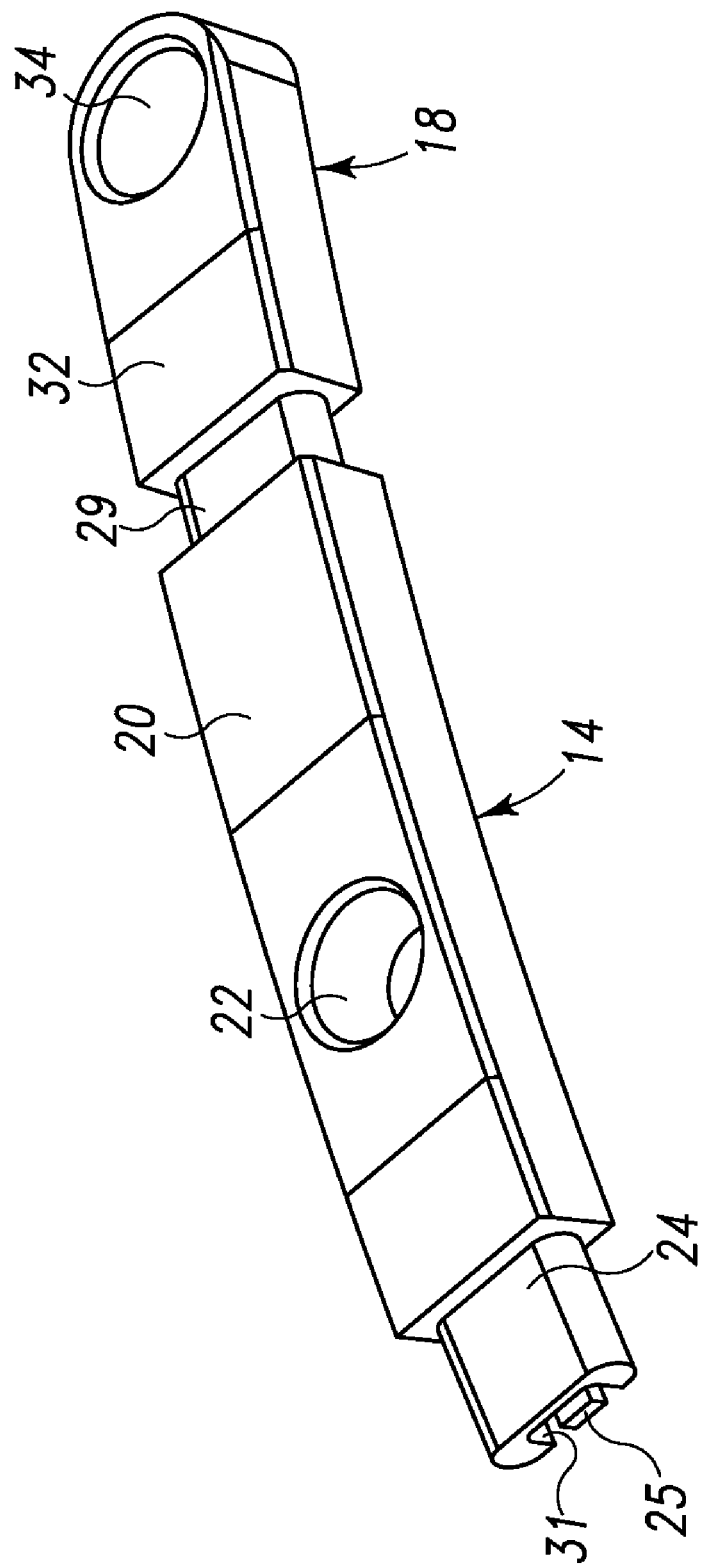
FIG. 7 is a perspective view of a middle spine plate component and end spine plate component of the single-sided dynamic spine plate of FIG. 1 shown in exploded view particularly illustrating the manner of connection between the middle spine plate component and the end spine plate component.

The middle component 14 is generally formed as an elongated rectangle that defines an outer, upper or anterior face or surface 20 and an inner, lower or posterior face or surface 21 wherein the surface 21 is configured to abut the outer surface of a vertebra. A bone screw bore 22 is formed in the middle component 14 for receipt of a bone screw (see, e.g. FIG. 8). The bone screw bore 22 may be configured to receive and lock a bone screw therein at a particular angle relative to the bone screw bore 22 and thus the spine plate 10. The middle component 14 includes a socket 19 on one end thereof and a flange 24 on another end thereof (see, e.g. FIGS. 3-7). Referring particularly to FIG. 7, the flange 24 includes a retention structure/mechanism formed as a resilient clip 25 on the end thereof, the clip 25 extending from a clip cavity 31 defined in the flange 24. The clip 25 is resiliently bendable such that it cooperates with a cutout to provide a snap fit/retention to an end component and/or another middle component should a multi-level dynamic single sided spine plate be desired. The socket 19 is sized to accommodate a flange 29 of the end component 18, the flange 29 being in like configuration to the flange 24 of the middle component 14 (and discussed further below). Moreover, the middle component 14 includes a cutout or slot 23 that is in communication with the cavity 19. The cutout 23 is sized to receive and retain a clip of a flange (e.g. clip 30 of flange 29 of the end component 18). The cutout 23 is sized in length to allow the flange to limitedly, axially move within the cutout 23 to allow the end component 18 to limitedly axially move relative to the middle component 14. The clip 30 is retained in the cutout 23 because of the resiliency of the clip 30 causing outward biasing thereof.

The end component 16 is generally formed as an elongated rectangle with one rounded end that defines an outer, upper or anterior face or surface 26 and an inner, lower or posterior face or surface 27 wherein the surface 27 is configured to abut the outer surface of a vertebra. A bone screw bore 28 is formed in or proximate to the rounded end of the end component 16 for receipt of a bone screw (see, e.g. FIG. 8). The bone screw bore 28 may be configured to receive and lock a bone screw therein at a particular angle relative to the bone screw bore 28 and thus the spine plate 10. The end component 16 includes a socket 36 on an end thereof (see, e.g. FIGS. 3-7) that is sized to receive a flange such as flange 24 of the middle component 14. The socket 36 is sized to accommodate the flange 24 of the middle component 14. The end component 16 includes a cutout or slot 35 that is in communication with the cavity 36. The cutout 35 is sized to receive and retain the clip of a flange (e.g. clip 25 of flange 24 of the middle component 14). The cutout 35 is sized in length to allow the flange 24 to limitedly, axially move within the cutout 35 to allow the end component 16 to limitedly axially move relative to the middle component 14. The clip 25 is retained in the cutout 35 because of the resiliency of the clip 25 causing outward biasing thereof.

The end component 18 is generally formed as an elongated rectangle with one rounded end that defines an outer, upper or anterior face or surface 32 and an inner, lower or posterior face or surface 33 wherein the surface 33 is configured to abut the outer surface of a vertebra. A bone screw bore 34 is formed in or proximate to the end component 18 for receipt of a bone screw (see, e.g. FIG. 8). The bone screw bore 34 may be configured to receive and lock a bone screw therein at a particular angle relative to the bone screw bore 34 and thus the spine plate 10. The end component 18 includes a flange 29 on an end thereof (see, e.g. FIGS. 3-7) that is sized to be received in a socket (e.g. the socket 19 of the middle component 14). The flange 29 includes a resilient clip 30 on the end thereof, the clip 30 extending from a clip cavity (not seen in the figures) defined in the flange 30 in like manner to the clip/clip cavity 25, 32 of the middle component 14. The clip 30 is resiliently bendable such that it cooperates with a cutout to provide a snap fit/retention to an end component and/or another middle component should a multi-level dynamic single sided spine plate be desired. The clip 30 of the end component 18 is received and retained in the cutout 23 of the middle component 14. The cutout 23 is sized in length to allow the flange 29 to limitedly, axially move within the cutout 23 to allow the end component 18 to limitedly axially move relative to the middle component 14. The clip 30 is retained in the cutout 23 because of the resiliency of the clip 30 causing outward biasing thereof.

As best seen in FIGS. 2-3 and 5-6, the spine plate 10 has rotation stabilizers that provide rotational stability to the spine plate 10 in addition to the bone screws that fasten the spine plate 10 to the vertebrae. While not shown, the other spine plate components may include rotation stabilizers about or proximate to one or all (any) bone screw holes. The spine plate 10 has first and second protrusions as rotation stabilizers, embodied as spikes 37, 38 on the dorsal end of the spine plate 10 and particularly the end component 16. The configuration of the rotational stabilizers may be different than spikes and encompass various cross-sectional patterns and/or shapes. The rotation stabilizers may be adjacent a screw hole and have a slightly different cross-section.

The spine plate 10 is curved as seen in FIG. 2 and represented by the double-headed, curved arrow. The curvature mimics the curvature of the spine/vertebrae to which the spine plate 10 will be attached.

FIGS. 4-6 depict the dynamic single sided spine plate 10 in an extended position. The extended position allows the axial or superior/inferior length of the spine plate 10 to be adjustable for implantation/fixation thereof and/or for allowing limited compression/extension of the vertebrae coupled by the spine plate 10 (i.e. superior/inferior movement). The double-headed arrows in FIG. 4 represent the individual ability of each one of the first and second end components 16, 18 to be adjustable/adjusted relative to the middle component 14 (and/or vice versa).

Figure 8:
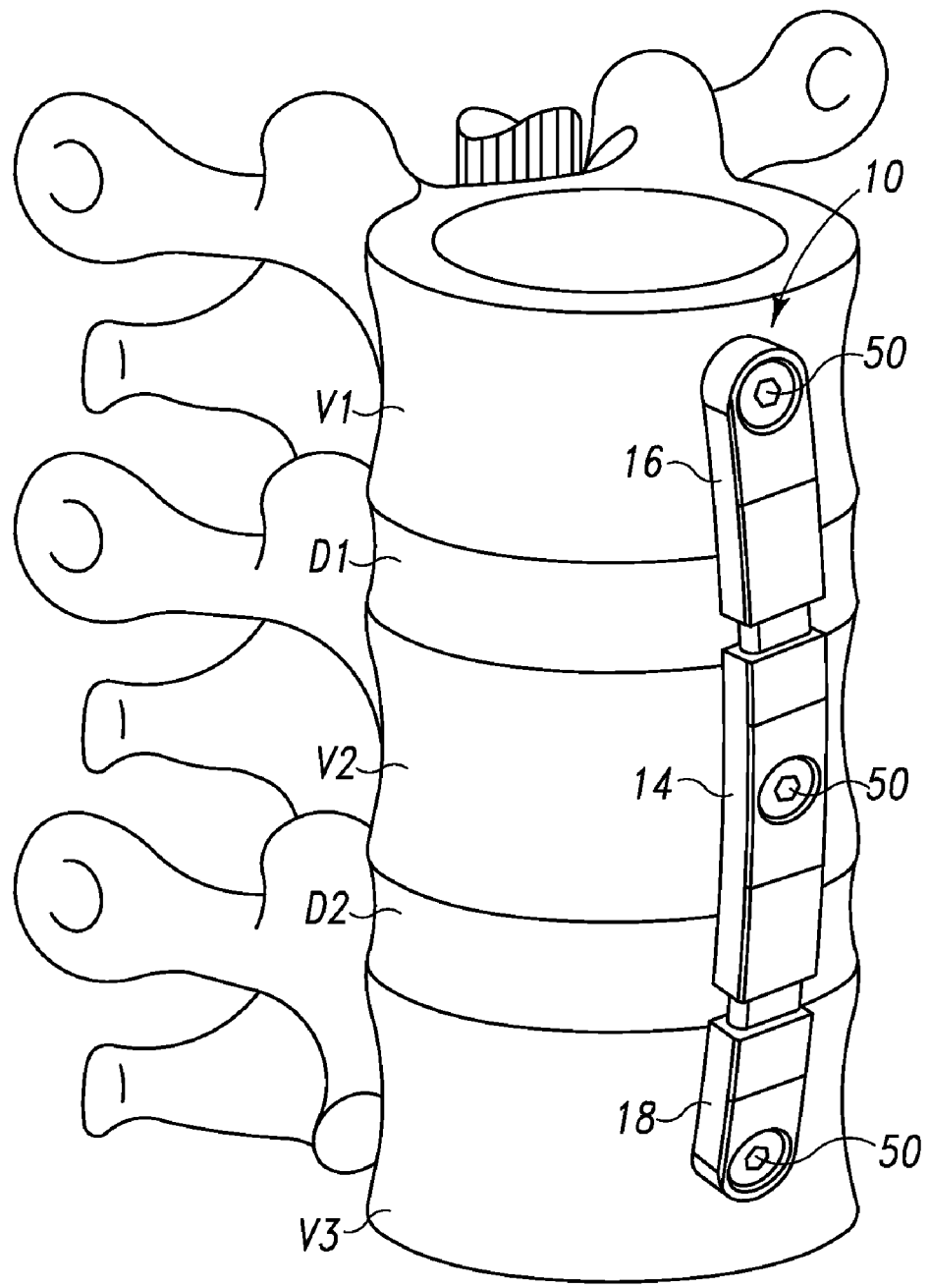
FIG. 8 is a perspective view of three vertebrae of a spine on which the single-sided dynamic spine plate of FIG. 1 is attached.
Figure 9:
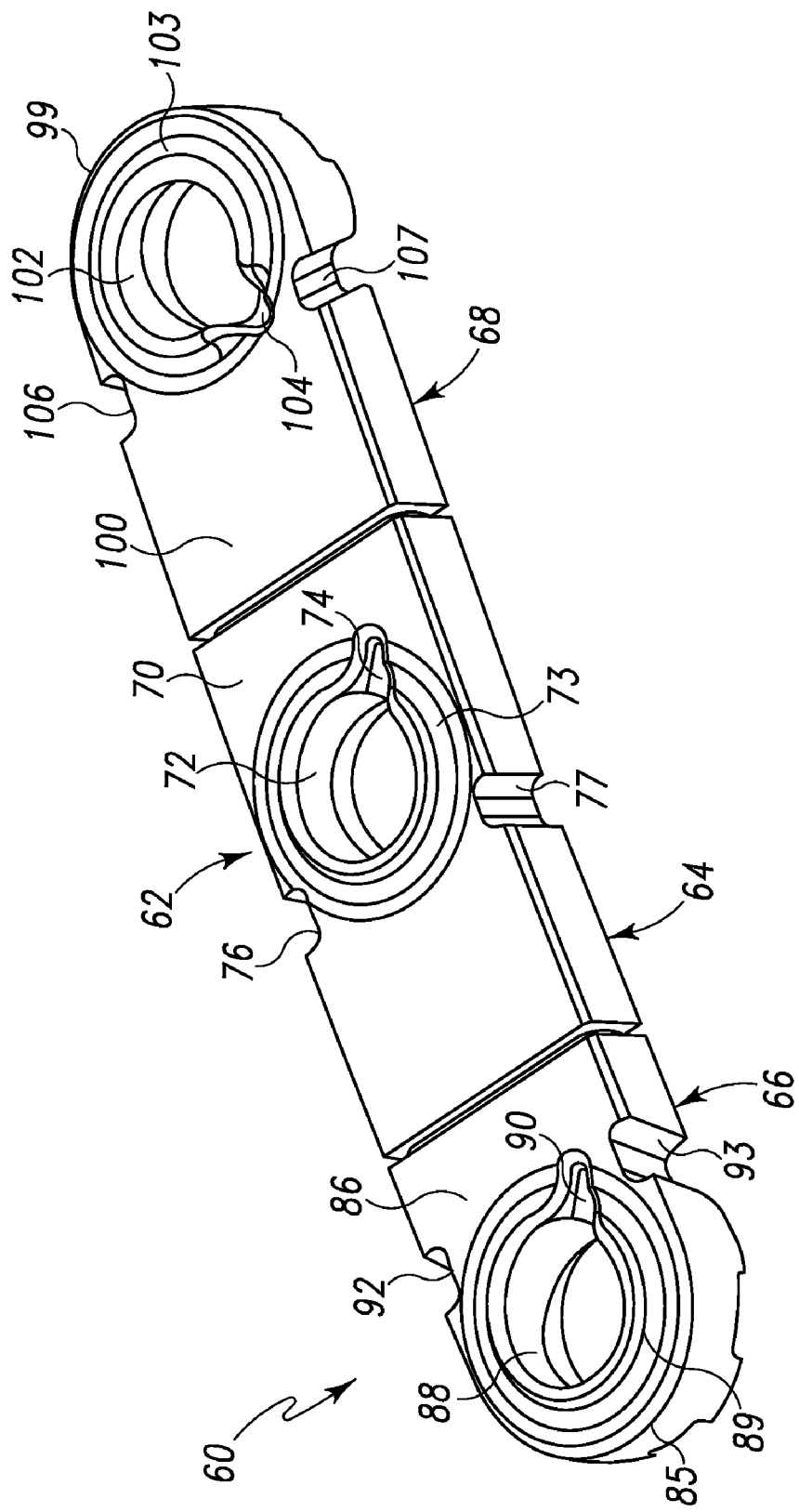
FIG. 9 is a perspective view of another embodiment of a single-sided dynamic spine plate fashioned in accordance with the present principles, the single-sided dynamic spine plate shown in an unexpanded, non-extended or closed position.
Figure 10:
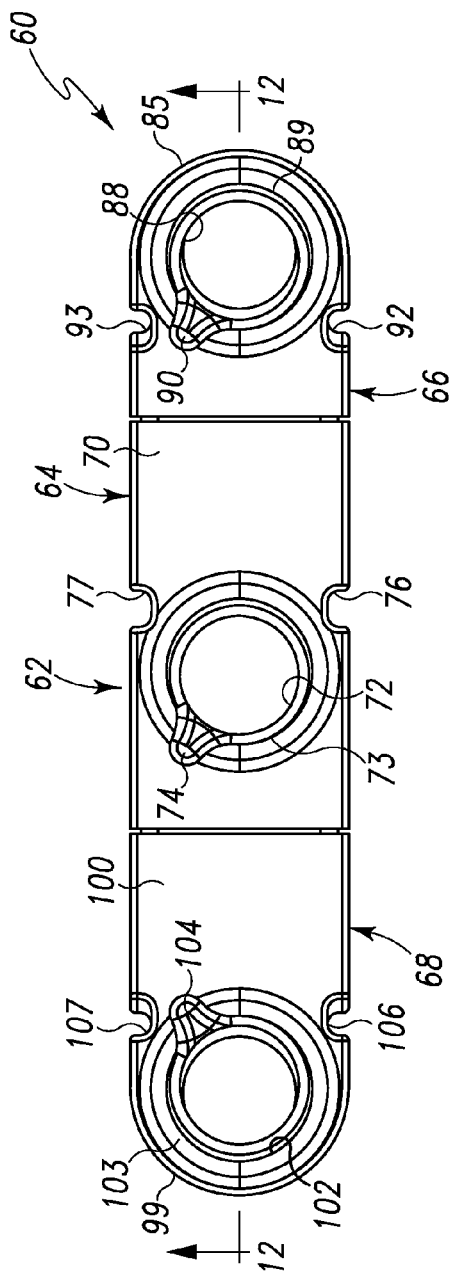
FIG. 10 is a top plan view of the single-sided dynamic spine plate of FIG. 9.
Figure 11:
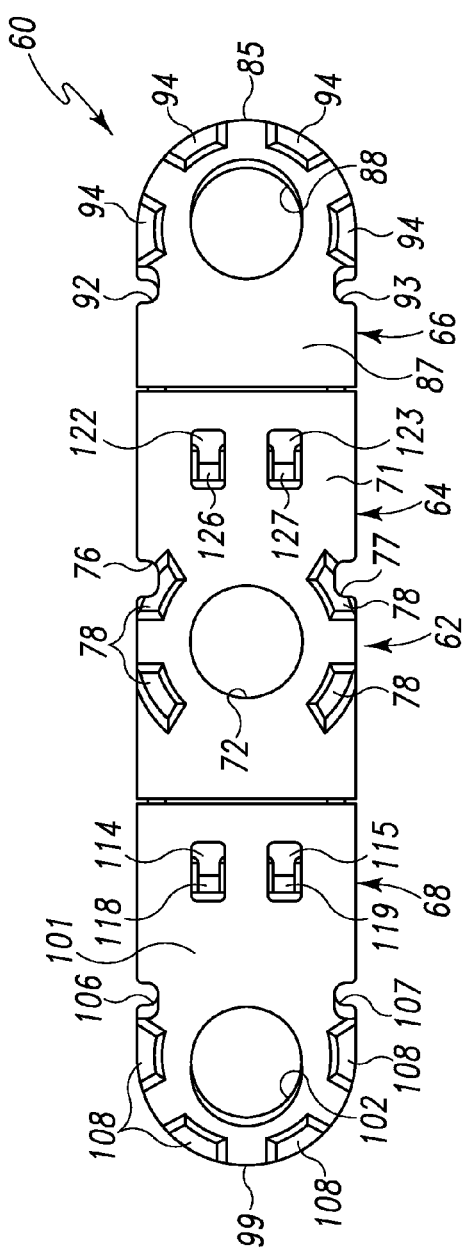
FIG. 11 is a bottom plan view of the single-sided dynamic plate of FIG. 9.

FIG. 8 depicts a portion of a spine and in particular three vertebrae labeled V1, V2 and V3 with the disc or disc space (with or without an implant) between adjacent vertebrae as D1 and D2. The vertebrae V1, V2, V3 may be any vertebrae of the spine such as the cervical, thoracic or lumbar vertebrae. Additionally, the number of vertebrae connected by the present spine plate 10 may be more or less than shown. It that regard, the appropriate level of spine plate is used. The single sided dynamic spine plate 10 is shown attached to a side (i.e. a single side) of the three vertebrae V1, V2, V3. It should be appreciated that placement of the spine plate 10 on the vertebrae V1, V2, V3 is exemplary, as various factors influence/determine proper placement.

Referring now to figures and particularly to FIGS. 9-20, there is depicted another embodiment of a single-sided dynamic spine plate generally designated 60. The single-sided dynamic spine plate 60 is formed of a suitable biocompatible material ("biomaterial") such as, for example, titanium, stainless steel, an alloy or the like. The single-sided dynamic spine plate 60 (spine plate 60) is characterized by a multi-component body 62 fashioned as an elongated rectangle. The spine plate 60 is shown as a two level (2-L) spine plate but may be fashioned as a single level (1-L) to a multi-level or n-level (n-L) spine plate in accordance with the present principles.

The body 62 is formed from a plurality of components and, in the embodiment shown in the figures, is formed of three components; a middle component, portion or section 64, a first end component, portion or section 66, and a second end component, portion or section 68. The body 62 defines a height or profile in like manner to the spine plate 10 of FIGS. 1-7 as shown in FIG. 2. As explained further below, the present spine plate 60 is dynamic in that it allows limited superior/inferior (axial) movement. In particular, the first and second end components 66, 68 are limitedly moveable relative to the middle component 64 (and/or the middle component 64 is movable relative to the first and second end components 66, 68. The spine plate 60 shown in FIGS. 9-12, however, is shown in a closed, un-extended or un-expanded position, wherein the first and second end components 66, 68 are abuttingly adjacent the middle component 64. In FIGS. 13-16 (discussed in detail below) the spine plate 60 is shown in an open, extended or expanded position wherein the first and second end components 66, 68 are a distance from the middle component 64. It should be appreciated that the open position shown in FIGS. 13-16 is only one open position of a possible plurality of open positions for the spine plate 60 (i.e. distances between the end components 66, 68 and the middle component 64). While the end components 66 and 68 are not identical or constitute the same piece, they may be interchangeable.

The middle component 64 is generally formed as an elongated rectangle that defines an outer, upper or anterior face or surface 70 and an inner, lower or posterior face or surface 71 wherein the surface 71 is configured to abut the outer surface of a vertebra. A bone screw bore 72 is formed in the middle component 64 for receipt of a bone screw. An annular depression 73 is formed about the bone screw bore 72. The bone screw bore 72 may be configured to receive and lock a bone screw therein at a particular angle relative to the bone screw bore 72 and thus the spine plate 60. A channel 74 is formed on one side of the annular depression 73. The channel 74 provides access for a tool to reach a head of a bone screw situated in the bone screw bore 72. A first notch 76 is provided on a first lateral side of the middle component 64 adjacent the bone screw bore 72, while a second notch 77 is disposed on a second lateral side of the middle component 64 adjacent the bone screw bore 72.

Figure 12:
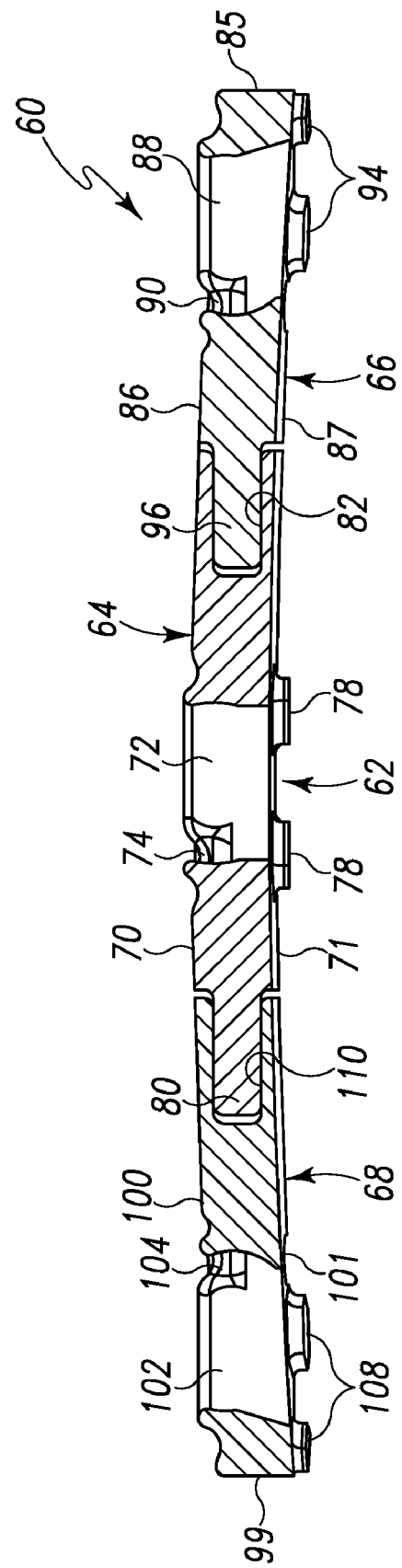
FIG. 12 is a sectional view of the single-sided dynamic spine plate of FIG. 9 taken along line 12-12 of FIG. 10.
Figure 13:
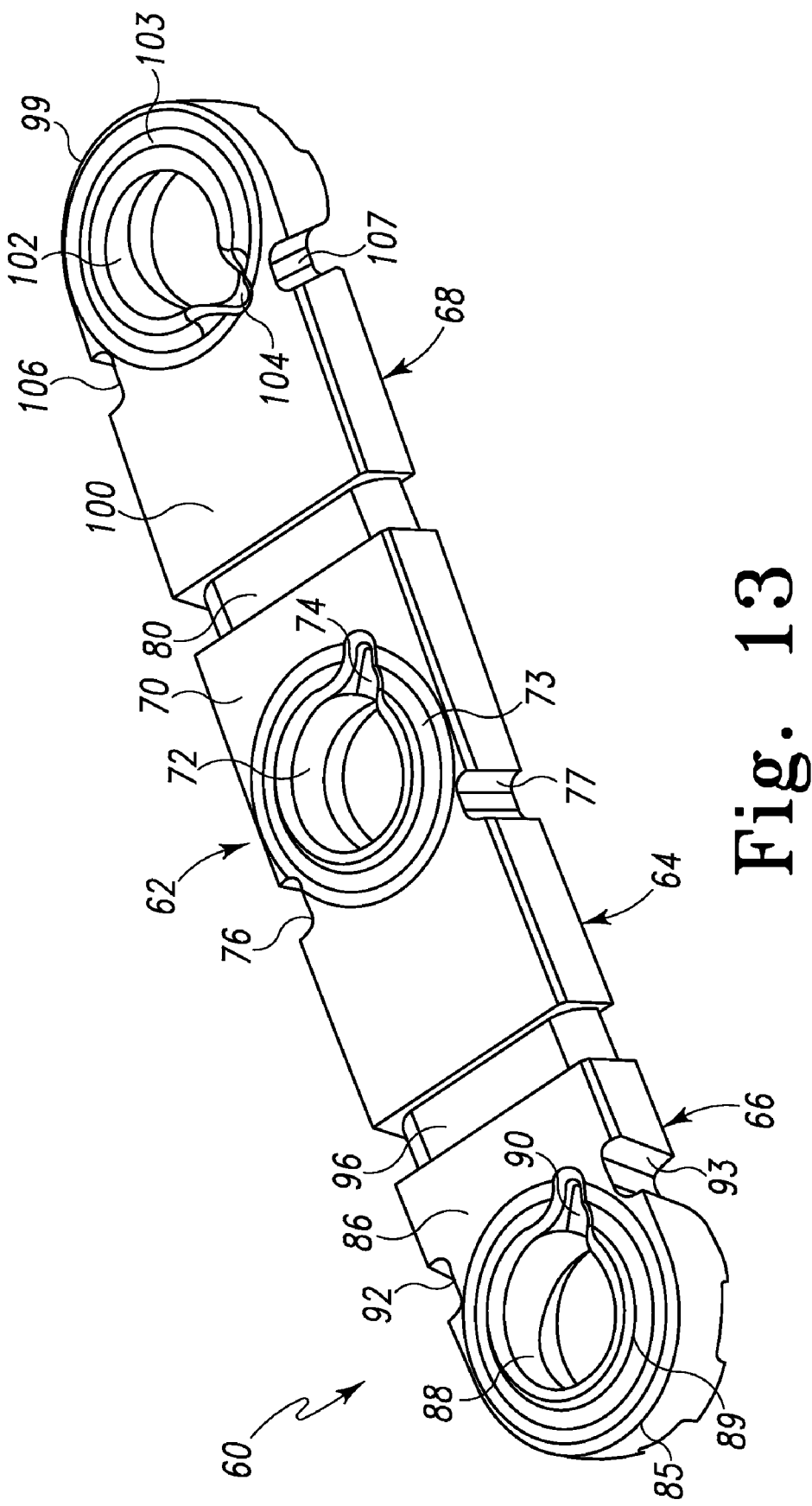
FIG. 13 is a perspective view of the single-sided dynamic spine plate of FIG. 9 shown in an expanded, extended or open position.
Figure 16:
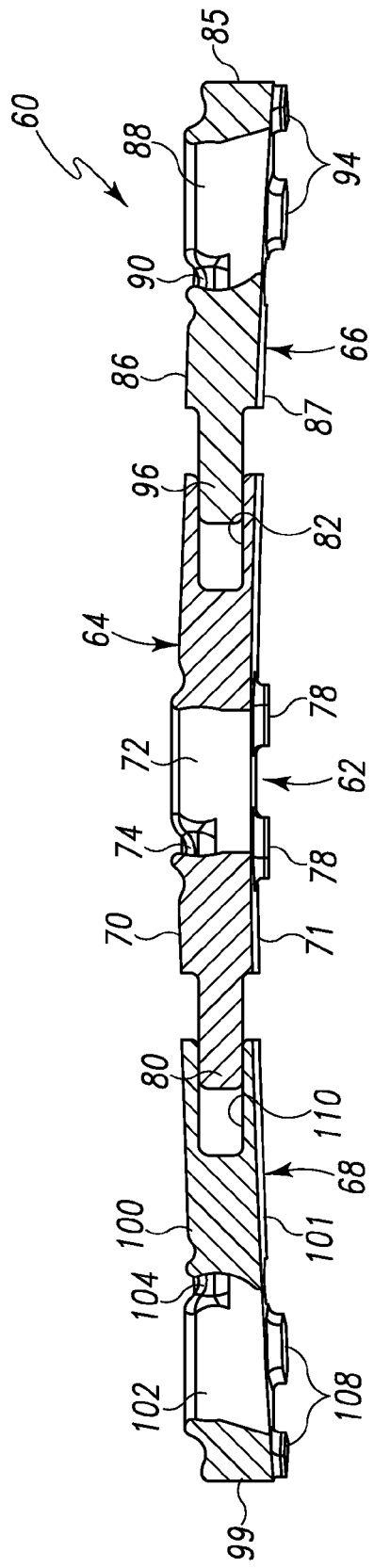
FIG. 16 is sectional view of the single-sided dynamic spine plate of FIG. 13 taken along line 16-16 of FIG. 14.
Figure 17:
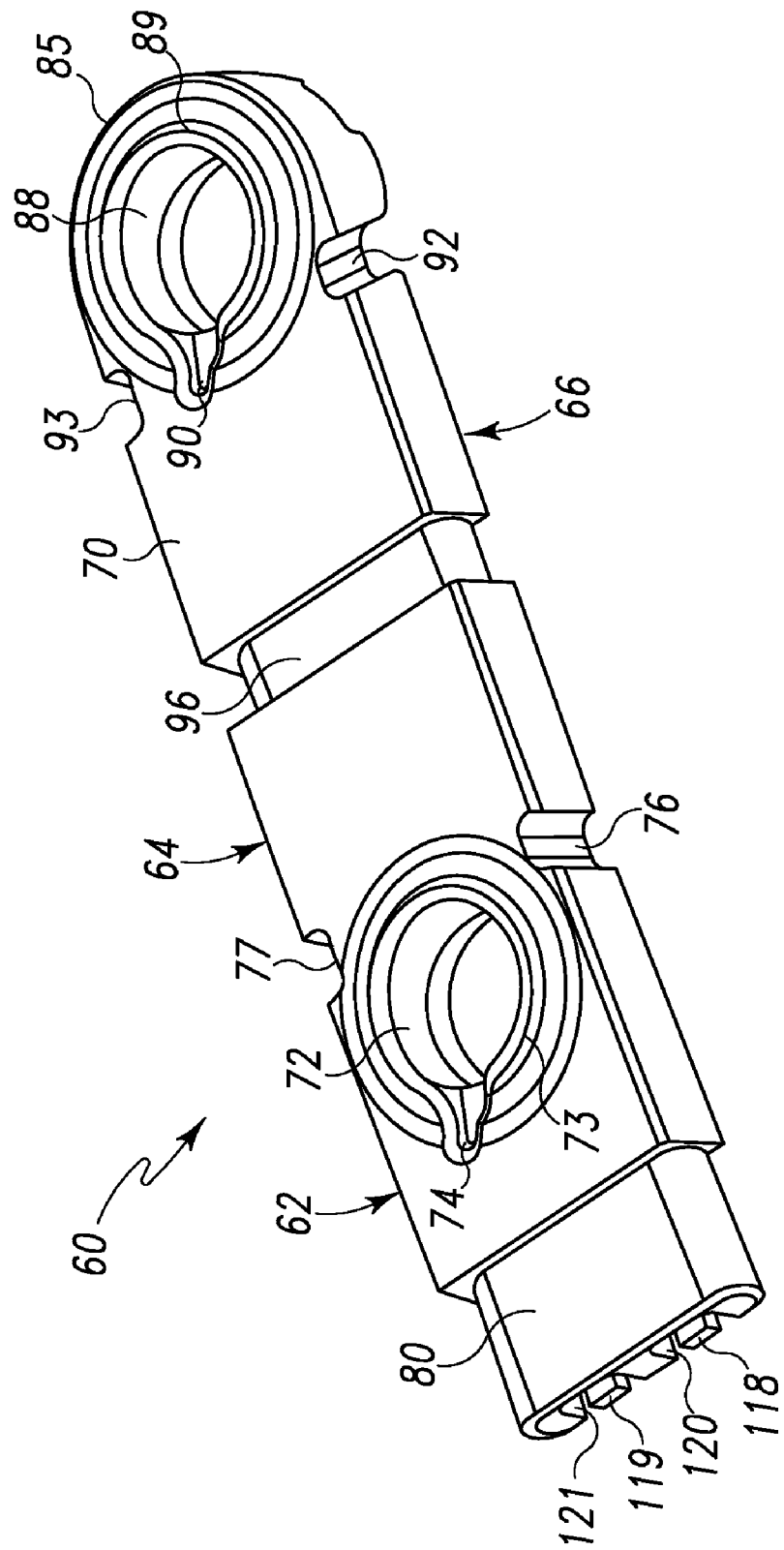
FIG. 17 is a perspective view of two components of the single-sided dynamic spine plate of FIG. 9 shown in an expanded, extended or open position.
Figure 18:
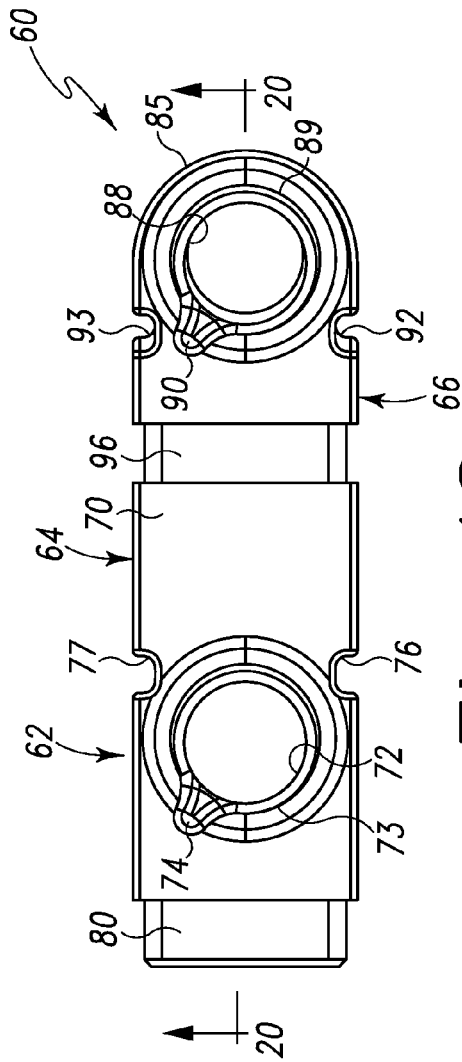
FIG. 18 is a top plan view of the single-sided dynamic spine plate of FIG. 17.
Figure 19:
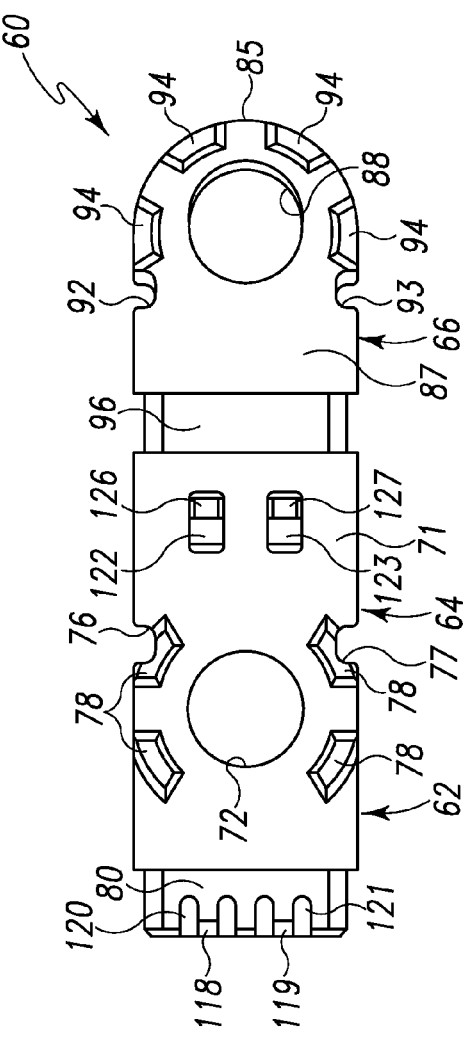
FIG. 19 is a bottom plan view of the single-sided dynamic spine plate of FIG. 17.
Figure 20:
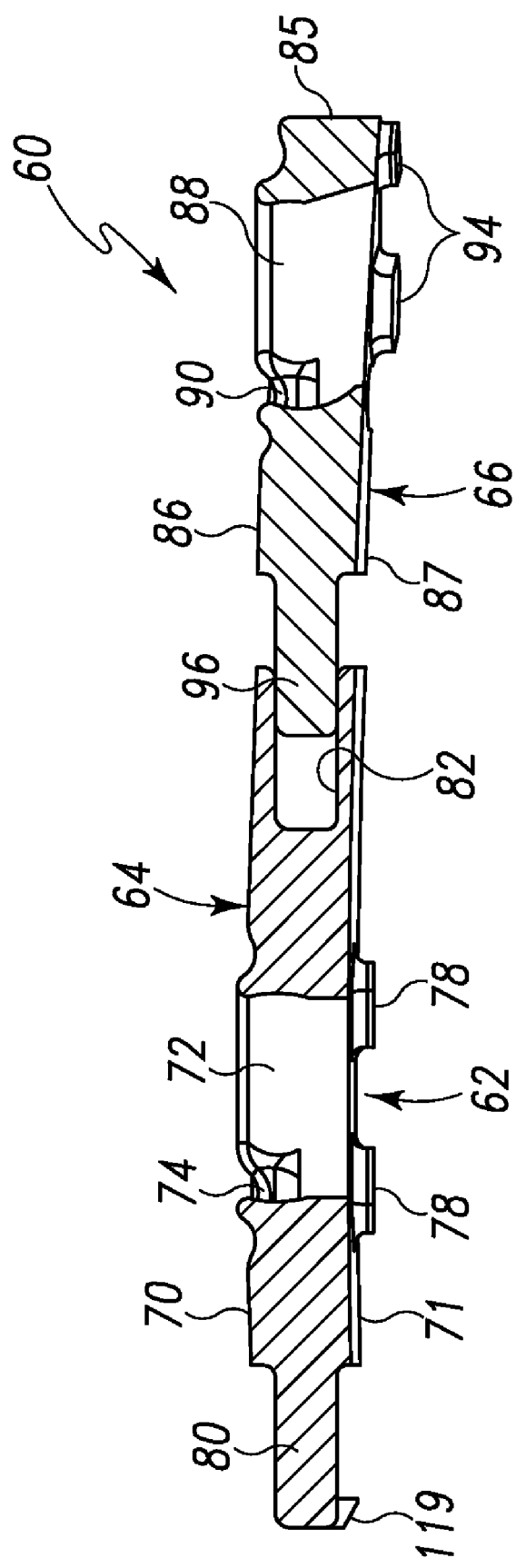
FIG. 20 is a sectional view of the single-sided dynamic spine plate of FIG. 17 taken along line 20-20 of FIG. 18.

The middle component 64 includes a flange 80 on one end thereof and a socket 82 on another end thereof (see, e.g. FIG. 12). Referring particularly to FIG. 17, the flange 80 includes a retention structure/mechanism formed as a first resilient clip 118 on the end thereof and a second resilient clip 120 on the end thereof. The first resilient clip 118 extends from a first clip cavity 119 defined in end of the flange 80 while the second resilient clip 120 extends from a second clip cavity 121. The first and second resilient clips 118, 120 are resiliently bendable such that each cooperates with a cutout, slot or opening (e.g. first and second cutouts 114, 115 of end component 68 that are in communication with the socket 110 thereof—see FIG. 11) to provide a snap fit/retention of the middle component 64 to the end component 68. The clips 118, 119 are limitedly movable within the cutouts 114, 115 of the end component 68 to provide limited axial movement between the middle and end components 64, 68 (i.e. the two components are dynamic).

The socket 82 is sized to accommodate a flange 96 of the end component 66, the flange 96 being in like configuration to the flange 80 of the middle component 64. Moreover, the middle component 64 includes first and second cutouts, slots or openings 122, 123 that are in communication with the socket or cavity 82. The cutouts 122, 123 each are sized to receive and retain a respective first and second clip 126, 127 of the flange 96 of the end component 66. The cutouts 122, 123 are sized in length to allow the clips 126, 127 to limitedly, axially move within the cutouts 122,123 to allow the flange 96 and thus the end component 66 to limitedly, axially move relative to the middle component 64. The clips 126, 127 are retained in the cutouts 122, 123 because of the resiliency of the clips 126, 127 causing outward biasing thereof.

The end component 66 is generally formed as an elongated rectangle with one rounded end that defines an outer, upper or anterior face or surface 86 and an inner, lower or posterior face or surface 87 wherein the surface 87 is configured to abut the outer surface of a vertebra. A bone screw bore 88 is formed in the end component 66 for receipt of a bone screw. An annular depression 89 is formed about the bone screw bore 88. The bone screw bore 72 may be configured to receive and lock a bone screw therein at a particular angle relative to the bone screw bore 88 and thus the spine plate 60. A channel 90 is formed on one side of the annular depression 89. The channel 90 provides access for a tool to reach a head of a bone screw situated in the bone screw bore 88. A first notch 92 is provided on a first lateral side of the end component 66 adjacent the bone screw bore 88, while a second notch 93 is disposed on a second lateral side of the end component 64 adjacent the bone screw bore 72. The bone screw bore 88 may be configured to receive and lock a bone screw therein at a particular angle relative to the bone screw bore 88 and thus the spine plate 60.

The end component 66 includes a flange 96 on an end thereof (see, e.g. FIGS. 3-7) that is sized to be received in the socket 82 of the middle component 64. The flange 96 of the end component 66 includes a retention structure/mechanism formed as a first resilient clip 126 on the end thereof and a second resilient clip 127 on the end thereof. The first resilient clip 126 extends from a first clip cavity (not seen) defined in end of the flange 80 while the second resilient clip 127 extends from a second clip cavity (not seen). The first and second resilient clips 126, 127 are resiliently bendable such that each cooperates with the first and second cutouts 122, 123 of the middle component 64 that are in communication with the socket 82 thereof—see FIG. 11) to provide a snap fit/retention of the middle component 64 to the end component 66. The clips 122, 123 are limitedly movable within the cutouts 122, 123 of the middle component 64 to provide limited axial movement between the middle and end components 64, 66 (i.e. the two components are dynamic). This movement defines a fully open or expanded position, a fully closed or unexpanded position, and positions intermediate the fully open and fully closed positions.

The end component 68 is generally formed as an elongated rectangle with one rounded end that defines an outer, upper or anterior face or surface 100 and an inner, lower or posterior face or surface 101 wherein the surface 101 is configured to abut the outer surface of a vertebra. A bone screw bore 102 is formed in the end component 68 for receipt of a bone screw. An annular depression 103 is formed about the bone screw bore 102. The bone screw bore 102 may be configured to receive and lock a bone screw therein at a particular angle relative to the bone screw bore 102 and thus the spine plate 60. A channel 103 is formed on one side of the annular depression 103. The channel 103 provides access for a tool to reach a head of a bone screw situated in the bone screw bore 102. A first notch 106 is provided on a first lateral side of the end component 68 adjacent the bone screw bore 102, while a second notch 107 is disposed on a second lateral side of the end component 68 adjacent the bone screw bore 102. The bone screw bore 102 may be configured to receive and lock a bone screw therein at a particular angle relative to the bone screw bore 102 and thus the spine plate 60.

The end component 68 includes a socket 110 on an end thereof (see FIG. 12) that is sized to receive a component flange (e.g. the flange 80 of the middle component 64). The socket 110 includes first and second cutouts, slots or openings 114, 115 that are in communication with the socket or cavity 110. The cutouts 114, 115 each are sized to receive and retain a respective first and second clip 118, 119 of the flange 80 of the middle component 64. The cutouts 114, 115 are sized in length to allow the clips 118, 119 to limitedly, axially move within the cutouts 114,115 to allow the flange 80 and thus the end component 68 to limitedly, axially move relative to the middle component 64. The clips 118, 119 are retained in the cutouts 114, 115 because of the resiliency of the clips 118, 119 causing outward biasing thereof.

As best seen in FIGS. 11-12 and 15-16, the spine plate 60 has rotation stabilizers that provide rotational stability to the spine plate 60 in addition to the bone screws that fasten the spine plate 60 to the vertebrae. The rotation stabilizers are situated on the undersides 71, 87 and 101 of the spine components 64, 66 and 68, and particularly about the bone screw bores 72, 88 and 102 of the spine components 64, 66 and 68. The rotation stabilizers are formed as angled, rectangular protrusions. Stabilizers 78 are situated about the bone screw bore 72 of the middle component 64 (see, e.g. FIG. 11), stabilizers 94 are situated about the bone screw bore 88 of the end component 66 (see, e.g. FIG. 11, and stabilizers 108 are situated about the bone screw bore 102 of the end component 68. Unlike the spine plate 10, the spine plate 60 is not curved. However, spine plate 60 may be curved if desired. Such The curvature would mimic the curvature of the spine/vertebrae to which the spine plate 60 would be attached.

FIGS. 13-16 depict the dynamic single sided spine plate 60 in an extended or open position. The extended position allows the axial or superior/inferior length of the spine plate 60 to be adjustable for implantation/fixation thereof and/or for allowing limited compression/extension of the vertebrae coupled by the spine plate 60 (i.e. superior/inferior movement). As can be discerned by referencing and comparing FIGS. 11 and 15, the end components 66 and 68 are dynamic or movable relative to the middle component 64 (and/or vice versa). Particularly, the first and second clips 126, 127 of the end component 66 are movable but constrained within the first and second slots 122, 123 of the socket 82 of the middle component 64. Thus, the end component 66 can move relative to the middle component 64 (or vice versa) the length of the movement of the first and second clips 126, 127 in the first and second slots 122, 123. The first and second clips 118, 119 of the middle component 64 are movable but constrained within the first and second slots 120, 121 of the socket 110 of the end component 66. Thus, the end component 66 can move relative to the middle component 64 (and vice versa) the length of the movement of the first and second clips 126, 127 in the first and second slots 122, 123. FIGS. 9-12 show the spine plate 60 in a fully closed position with both of the end components 66, 68

FIGS. 17-20 depict the middle component 64 and the end component 66 of the spine plate 60. These views provide detail of the clips of the flanges of the plate components. The end component 66 is shown in a fully expanded position relative to the middle component 64. The underside of the flange 80 of the middle component 64 is depicted that particularly shows the resilient clip 118 situated within the cavity 120 and the resilient clip 119 situated within the cavity 121. It should be appreciated that more than two clips and cutouts may be used.

Figure 21:
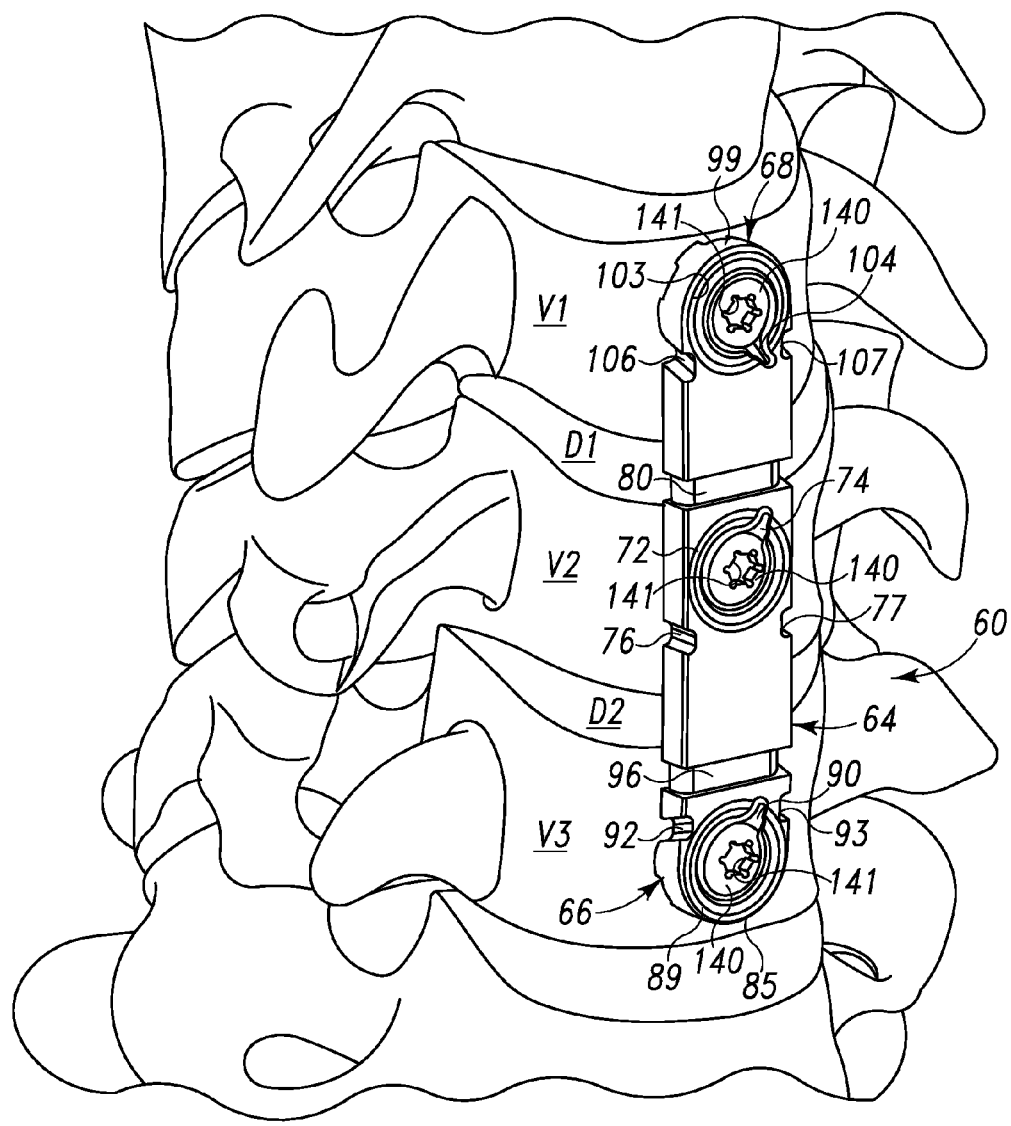
FIG. 21 is a perspective view of three vertebrae of a spine on which the single-sided dynamic spine plate of FIG. 9 is attached.

FIG. 21 depicts a portion of a spine and in particular three vertebrae labeled V1, V2 and V3 with the disc or disc space (with or without an implant) between adjacent vertebrae as D1 and D2. The vertebrae V1, V2, V3 may be any vertebrae of the spine such as the cervical, thoracic or lumbar vertebrae. Additionally, the number of vertebrae connected by the present spine plate 10 may be more or less than shown. It that regard, the appropriate level of spine plate is used. The single sided dynamic spine plate 60 is shown attached to a side (i.e. a single side) of the three vertebrae V1, V2, V3. It should be appreciated that placement of the spine plate 60 on the vertebrae V1, V2, V3 is exemplary, as various factors influence/determine proper placement.

While the invention has been illustrated and described in detail in the drawings and foregoing description, the same is to be considered as illustrative and not restrictive in character, it being understood that only preferred embodiments have been shown and described and that all changes and modifications that come within the spirit of the invention are desired to be protected.

What is claimed is:

1. A spine plate for attachment to a first vertebra, a middle vertebra, and a second vertebra, the spine plate comprising:
    a middle component having a single fastening element for allowing attachment of the middle component to a middle vertebra;
    a first end component dynamically coupled to an end of the middle component to guide movement toward and away from the middle component and having only a single fastening element for allowing attachment of the first end component to the first vertebra adjacent the middle vertebra, and a pair of spaced apart spikes extending from a posterior surface of the first end component and located on opposite sides of the single fastening element; and
    a second end component dynamically coupled to another end of the middle component to guide movement toward and away from the middle component and having only a single fastening element for allowing attachment of the second end component to the second vertebrae adjacent the middle vertebra;
    wherein the middle component includes a first vertical notch located on a first lateral side and a second vertical notch located on a second lateral side opposite the first lateral side and extending between anterior and posterior surfaces;
    wherein the first end component includes a first angled notch located on a first lateral side extending between anterior and posterior surfaces, and a second angled notch located on a second lateral side opposite the first lateral side and extending between anterior and posterior surfaces.

2. The spine plate of claim 1, wherein each single fastening element comprises a bone screw bore.

3. A spine plate for attachment to a first vertebra, a middle vertebra, and a second vertebra, the spine plate comprising:
    a middle component having only a single fastening element for allowing attachment of the middle component to the middle vertebra;
    a first end component dynamically coupled to an end of the middle component to guide movement toward and away from the middle component and having only a single fastening element for allowing attachment of the first end component to the first vertebra adjacent the middle vertebra, and a pair of spaced apart spikes extending from a posterior surface of the first end component and located on opposite sides of the single fastening element; and
    a second end component dynamically coupled to another end of the middle component to guide movement toward and away from the middle component and having only a single fastening element for allowing attachment of the second end component to the second vertebrae adjacent the middle vertebra;
    wherein each single fastening element comprises a bone screw bore;
    wherein the middle component comprises a channel in the anterior surface extending radially out from the bone screw bore;
    wherein the first end component comprises a channel in the anterior surface extending radially out from the bone screw bore; and
    wherein the second end component comprises a channel in the anterior surface extending radially out from the bone screw bore.

4. The spine plate of claim 3, wherein the middle component includes a first vertical notch located on a first lateral side and a second vertical notch located on a second lateral side opposite the first lateral side and extending between anterior and posterior surfaces.

5. The spine plate of claim 4, wherein the first end component includes a first angled notch located on a first lateral side extending between anterior and posterior surfaces, and a second angled notch located on a second lateral side opposite the first lateral side and extending between anterior and posterior surfaces.

6. The spine plate of claim 5, wherein the second end component includes a first angled notch located on a first lateral side extending between anterior and posterior surfaces, and a second angled notch located on a second lateral side opposite the first lateral side and extending between anterior and posterior surfaces.

7. The spine plate of claim 3, wherein the first, second and third plurality of rotation stabilizers comprise configured protrusions.

8. A spine plate comprising:
    a middle component having only a single fastening element for allowing attachment of the middle component to a middle vertebra, a first middle component connector at a first end thereof and a second middle component connector at a second end thereof, the middle component having a plurality of angled rectangular stabilizer protrusions spaced apart radially about the single fastening element;

a first end component having only a single fastening element for allowing attachment of the first end component to a first vertebra adjacent the middle vertebra and a first end component connector configured for dynamic attachment to the first middle component connector that allows guides movement toward and away from the middle component, the first end component having a plurality of angled rectangular stabilizer protrusions spaced apart radially about the single fastening element; and a second end component having only a single fastening element for allowing attachment of the second end component to a second vertebra adjacent the middle vertebra and a second end component connector configured for dynamic attachment to the second middle component connector that allows guides movement toward and away from the middle component.

9. The spine plate of claim 8, wherein the component connectors are one of a socket and flange.

10. The spine plate of claim 9, wherein:
each socket includes a slot formed in a lower surface of the socket; and
each flange includes a resilient clip configured for receipt in a slot of a socket.

11. The spine plate of claim 9, wherein:
each socket includes two slots formed in a lower surface of the socket; and
each flange includes a two resilient clips configured for receipt in the two slots of a socket.

12. The spine plate of 8, wherein each single fastening element comprises a bone screw bore.

13. The spine plate of claim 8, wherein the middle component includes a first vertical notch located on a first lateral side and a second vertical notch located on a second lateral side opposite the first lateral side and extending between anterior and posterior surfaces.

14. The spine plate of claim 13, wherein the first end component includes a first angled notch located on a first lateral side extending between anterior and posterior surfaces, and a second angled notch located on a second lateral side opposite the first lateral side and extending between anterior and posterior surfaces.

15. The spine plate of claim 14, wherein the second end component includes a first angled notch located on a first lateral side extending between anterior and posterior surfaces, and a second angled notch located on a second lateral side opposite the first lateral side and extending between anterior and posterior surfaces.

16. The spine plate of claim 8, wherein:
the middle component comprises a channel in the anterior surface extending radially out from the bone screw bore;
the first end component comprises a channel in the anterior surface extending radially out from the bone screw bore; and
the second end component comprises a channel in the anterior surface extending radially out from the bone screw bore.

17. A spine plate comprising:
a middle component having only a single bone screw bore for allowing attachment of the middle component to a middle vertebra, a middle component socket at a first end thereof and a middle component flange at a second end thereof, the middle component having a first vertical notch located on a first lateral side and a second vertical notch located on a second lateral side opposite the first lateral side and extending between anterior and posterior surfaces;
a first end component having only a single bone screw bore for allowing attachment of the first end component to a first vertebra adjacent the middle vertebra and a first end connector flange configured for dynamic attachment to the middle component socket that allows expansion and compression relative to the middle component, the first end component having a first angled notch located on a first lateral side extending between anterior and posterior surfaces, and a second angled notch located on a second lateral side opposite the first lateral side and extending between anterior and posterior surfaces; and
a second end component having only a single bone screw bore for allowing attachment of the second end component to a second vertebra adjacent the middle vertebra and a second end component socket configured for dynamic attachment to the middle component flange that allows expansion and compression relative to the middle component, the second end component having a first angled notch located on a first lateral side extending between anterior and posterior surfaces, and a second angled notch located on a second lateral side opposite the first lateral side and extending between anterior and posterior surfaces.

18. The spine plate of claim 17, wherein:
each socket includes two slots formed in a lower surface of the socket; and
each flange includes a two resilient clips configured for receipt in the two slots of a socket.

19. The spine plate of claim 18, wherein ends of the first angled notches proximate the anterior surface are closer to the middle component than the ends of the first angled notches proximate the posterior surface.

\* \* \* \* \*